(12) United States Patent
Rossing

(10) Patent No.: US 9,026,215 B2
(45) Date of Patent: May 5, 2015

(54) HYPERTENSION TREATMENT DEVICE AND METHOD FOR MITIGATING RAPID CHANGES IN BLOOD PRESSURE

(75) Inventor: Martin A. Rossing, Coon Rapids, MN (US)

(73) Assignee: CVRx, Inc., Minneapolis, MN (US)

( * ) Notice: Subject to any disclaimer, the term of this patent is extended or adjusted under 35 U.S.C. 154(b) by 2120 days.

(21) Appl. No.: 11/323,565

(22) Filed: Dec. 29, 2005

(65) Prior Publication Data

US 2007/0156201 A1     Jul. 5, 2007

(51) Int. Cl.
    *A61N 1/36*     (2006.01)

(52) U.S. Cl.
    CPC ......... *A61N 1/36114* (2013.01); *A61N 1/36117* (2013.01)

(58) Field of Classification Search
    CPC .................................................. A61N 1/36117
    USPC ........................................................... 607/44
    See application file for complete search history.

(56) References Cited

U.S. PATENT DOCUMENTS

| | | | |
|---|---|---|---|
| 3,650,277 A * | 3/1972 | Sjostrand et al. | ............... 607/44 |
| 5,707,400 A | 1/1998 | Terry, Jr. et al. | |
| 6,073,048 A | 6/2000 | Kieval et al. | |
| 6,522,926 B1 | 2/2003 | Kieval et al. | |
| 6,529,771 B1 | 3/2003 | Kieval et al. | |
| 2005/0149130 A1 | 7/2005 | Libbus | |
| 2005/0149143 A1 * | 7/2005 | Libbus et al. | ................... 607/44 |

OTHER PUBLICATIONS

Repeated Ambulatory Monitoring Reveals a Monday Morning Surge in Blood Pressure in a Community-Dwelling Population. Murakami S, Otsuka K., Kubo Y et al., 17 Am J Hypertens. 1179-83 (2004).
Morning Surge in Blood Pressure as a Predictor of Silent and Clinical Cerebrovascular Disease in Elderly Hypertensives: Kazuomi Kario et al., A Prospective Study. 107 Circulation 2003; 107; 1401-06 (2003).
Morning Surge in Blood Pressure. Norman M. Kaplan. American Heart Association. Circulation 2003; 107; 1347.

* cited by examiner

*Primary Examiner* — Eric D. Bertram
(74) *Attorney, Agent, or Firm* — Patterson Thuente Pedersen, P.A.

(57) ABSTRACT

An implantable baroreflex activation device administers a special electrotherapy program that causes the device to apply electrotherapy to limit a rate of change of blood pressure increase associated with a blood pressure surge event such as a morning blood pressure surge (MBPS).

9 Claims, 18 Drawing Sheets

HYPERTENSION TREATMENT DEVICE AND METHOD FOR MITIGATING RAPID CHANGES IN BLOOD PRESSURE

BACKGROUND OF THE INVENTION

Field of the Invention

The present invention relates generally to medical devices and treatment and, more particularly, to electrotherapeutic treatment of rapid changes in blood pressure.

Cardiovascular disease is a major contributor to patient illness and mortality. It also is a primary driver of health care expenditure, costing more than $326 billion each year in the United States. Hypertension, or high blood pressure, is a major cardiovascular disorder that is estimated to effect over 50 million people in the United Sates alone. Of those with hypertension, it is reported that fewer than 30% have their blood pressure under control. Hypertension is a leading cause of heart failure and stroke. It is the primary cause of death in over 42,000 patients per year and is listed as a primary or contributing cause of death in over 200,000 patients per year in the U.S. Accordingly, hypertension is a serious health problem demanding significant research and development for the treatment thereof.

Hypertension may occur when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year. It is also estimated that greater than 400,000 new cases of heart failure are diagnosed each year. Heart failure accounts for over 900,000 hospital admissions annually, and is the most common discharge diagnosis in patients over the age of 65 years. It has been reported that the cost of treating heart failure in the United States exceeds $20 billion annually. Accordingly, heart failure is also a serious health problem demanding significant research and development for the treatment and/or management thereof.

Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state.

The body's systems responsible for control of blood pressure respond to the overall activity level of the body. Typically, these systems cause a daily increase in blood pressure to accompany the change in activity levels as the body transitions from a sleeping state to an active state. The incidence of acute cardiovascular events, such as myocardial infarction (heart attacks), sudden cardiac death, and stroke, is known to increase during the morning hours and is usually attributed to the surge in early-morning blood pressure. Weekly variations, peaking on Mondays, have also been reported, which may account for the higher frequency of cardiovascular events on Mondays. See Murakami S, Otsuka K, Kubo Y, et al., Repeated ambulatory monitoring reveals a Monday morning surge in blood pressure in a community-dwelling population, 17 Am J Hypertens. 1179-83 (2004). Morning surges in blood pressure have also been linked to strokes in the elderly. Kazuomi Kario, et al., Morning Surge in Blood Pressure as a Predictor of Silent and Clinical Cerebrovascular Disease in Elderly Hypertensives: A Prospective Study, 107 Circulation 1401-06 (2003).

It has been known for decades that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through activation of the sympathetic nervous system.

Electrical stimulation of the carotid sinus nerve (baropacing) has previously been proposed to reduce blood pressure and the workload of the heart in the treatment of high blood pressure and angina. For example, U.S. Pat. No. 6,073,048 to Kieval et al., which is incorporated by reference herein in its entirety, discloses a baroreflex modulation system and method for stimulating the baroreflex arc based on various cardiovascular and pulmonary parameters. Other implantable devices for treating or monitoring high blood pressure or hypertension by stimulating various nerves and tissue in the body are known and described, for example, in U.S. Pat. No. 3,650,277 (stimulation of carotid sinus nerve), U.S. Pat. No. 5,707,400 (stimulation of vagal nerve), U.S. Pat. No. 6,522,926 (stimulation of baroreceptors), and U.S. Pat. No. 6,529,771 (monitoring of patient cardiac status), all of which are incorporated by reference herein in their entirety.

These, and other implantable electrotherapeutic hypertension treatments can control blood pressure by influencing the body's sense-response system. Electrotherapy techniques can include fixed, continuous monotherapy to effectuate an across-the-board reduction in blood pressure, or dynamic therapy, in response to sensed blood pressure or activity level, to effectuate condition- or demand-based blood pressure control. U.S. Patent Application Publication No. 2005/0149130, which is incorporated by reference herein in its entirety, discusses adapting electrotherapy for hypertension treatment according to the patient's circadian rhythm.

One drawback of existing hypertension electrotherapy systems is these systems are not especially adapted to address the problem of morning blood pressure surges, which, due to their apparent propensity for triggering severe catastrophic cardiovascular events, merit specialized management for minimizing their adverse effects.

BRIEF SUMMARY OF THE INVENTION

One aspect of the present invention is directed to a hypertension treatment device that administers electrostimulation to a patient's baroreceptors to selectively control blood pressure in the patient, wherein the administration of the electrostimulation is based, at least in part, on the time of day. Preferably, the electrostimulation is administered by the hypertension treatment device according to a profile that is designed to reduce the severity of surges in morning blood pressure surges (MBPS) of the patient by reducing the time-rate-of-change of these morning surges.

According to one embodiment, a hypertension treatment device implanted in a patient includes a time base clock. One embodiment of the time base clock is a real-time clock circuit that is configured to represent at least the time of day. Preferably, the time base clock can also represent the day of the week. The device is configured with a first transition time setting at which the patient is anticipated to transition from a state of relative inactivity to a state of relatively higher activity. In operation, the device executes a special electrotherapy program during a time window proximate in time to the first transition time setting. Preferably, the start of the time window precedes the first transition time setting, and the end of the time window succeeds the first transition time setting.

The special electrotherapy program causes the device to selectively apply electrostimulation such that the patient's blood pressure rises relatively gradually in response to a low-to-high activity level transition occurring proximately in time to the first transition time setting. The relatively gradual blood pressure rise is relative to the rise that would occur in the absence the special electrotherapy program, and can be achieved by reducing the difference between the low-pressure and high-pressure levels, by extending the time duration during which the blood pressure rise occurs, or by a combination thereof.

According to one embodiment, as the time of day approaches the transition time setting, (i.e., towards the end of the period of relative inactivity, but before the start of the transition to the period of higher activity of the patient), the special electrotherapy program either permits, or initiates, the patient's blood pressure to rise, respectively, by either reducing the level of pressure-reducing electrotherapy, or by applying pressure-increasing electrotherapy. In a related embodiment, following the transition time setting, the special electrotherapy program administers pressure-reducing electrotherapy. Preferably, the level of pressure-reducing electrotherapy administered soon after the transition time setting by the special electrotherapy program is greater than a nominal level of electrotherapy applied outside of the time window of the special electrotherapy program.

In various embodiments, the hypertension treatment device incorporates one or more sensors to facilitate heuristically determining the transition time setting, recognizing the patient's actual transition from low- to high-activity levels, and measuring the intensity of a surge in the patient's blood pressure as part of a control loop that regulates the levels of electrotherapy to apply during the special electrotherapy program. The sensor(s) can work in conjunction with, or independently from, the real-time clock-related functionality of the hypertension treatment device.

In a related embodiment, the hypertension treatment device includes a communications circuit for interfacing with an external programmer. In one embodiment, the programmer is integral with an appliance or instrument used daily by the patient, such as an alarm clock, wherein its use pattern is predictive of the patient's actual transition time. The programmer can set or adjust the transition time setting.

Figure 1:
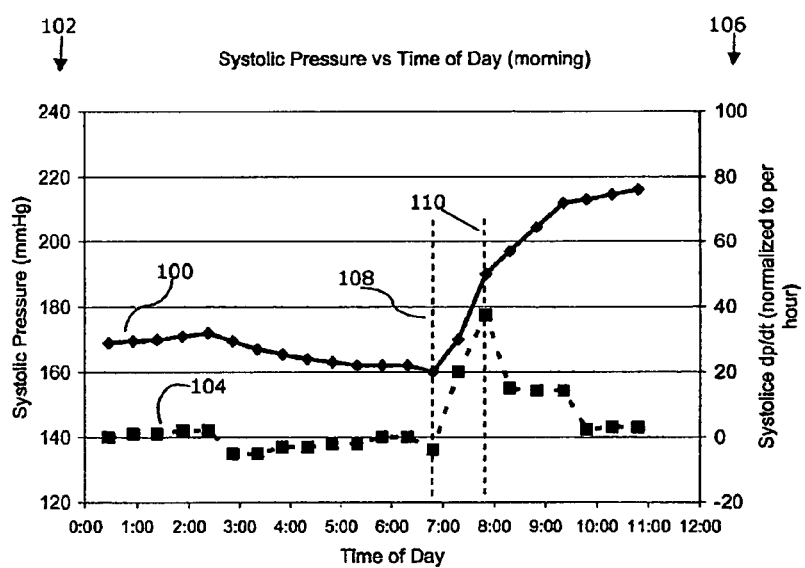
FIG. 1 is a diagram illustrating a morning blood pressure surge (MBPS) in a patient, and includes curves representing the systolic blood pressure as a function of time, and the rate of change of the systolic blood pressure, normalized to dP/dt per hour.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

FIG. 1 shows a curve illustrating a typical systolic blood pressure profile for a hypertension patient during the morning hours. Curve 100 is plotted against vertical access 102 and represents the patient's systolic blood pressure in mmHg. Curve 104 represents the rate of change of curve 100 and is plotted against vertical access 106, which is normalized to mmHg per hour. As can be seen from curves 100 and 104, a transition point 108 exists just before 7:00. Transition point 108 coincides with the time when the patient awakens from a sleep state and transitions from a state of relatively low activity to a period of relatively higher activity level.

Beginning at transition point 108, curve 100 depicts the patient's blood pressure rising sharply from about 160 mmHg to nearly 120 mmHg. This phenomenon is known as the morning blood pressure surge (MBPS) and, as described above, has been associated with the incidents of heart attacks, strokes, and other catastrophic cardiovascular events. The patient's blood pressure increases at a rapid rate until about 9:15, and then stabilizes at its final level. The rate of blood pressure increase peaks between 7:30 and 8:00 at about 40 mmHg per hour, as indicated at 110.

One aspect of the present invention is directed to an electrotherapy method and apparatus for reducing severity of the MBPS. Reducing the severity of the MBPS can include slowing the rate of blood pressure increase associated with the surge, reducing the difference between the pre-surge and post-surge blood pressure levels, or administering a treatment that is a combination thereof.

Figure 2A:
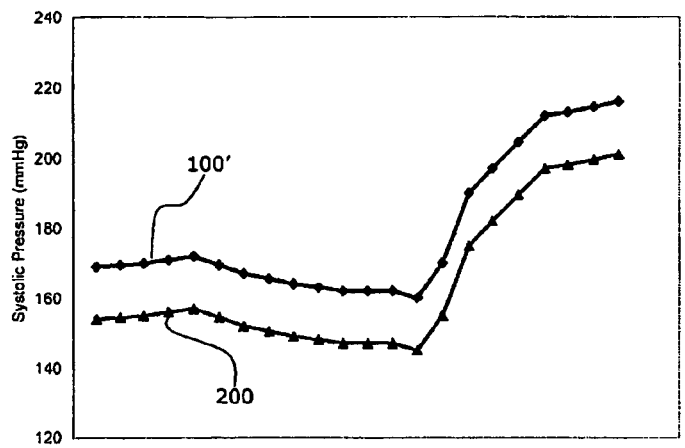
FIGS. 2A through 2C illustrate the effect of conventional electrotherapy of a continuous fixed level (monotherapy) on a patient's systolic blood pressure curve during the MBPS.
Figure 2B:
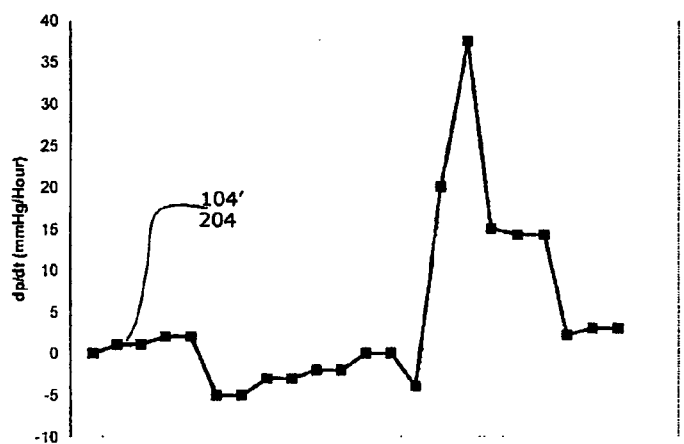
Figure 2C:
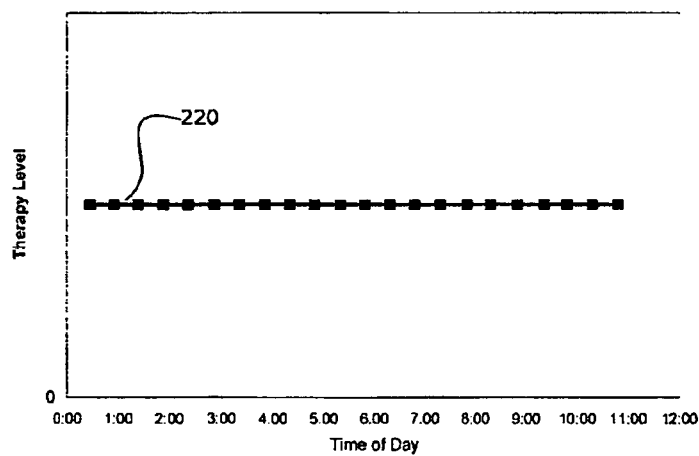

FIGS. 2A through 2C illustrate the effect of conventional electrotherapy of a continuous fixed level (monotherapy) on a patient's systolic blood pressure curve during the MBPS. As shown in FIG. 2A, curve 100' is the same as 100 of FIG. 1 and represents the patient's blood pressure pattern in the absence of any electrotherapy. Curve 200 of FIG. 2A represents the patient's blood pressure pattern over the same time period and while the patient receives a constant level of pressure-reducing electrotherapy. The therapy level is illustrated as a function of time at curve 220 in FIG. 2C. As can be seen in FIG. 2A, the monotherapy provides a constant reduction in blood pressure throughout the time period shown. While the blood pressure pattern depicted by curve 200 is overall lower than blood pressure pattern 100', the MBPS between the two curves has an identical rate of change profile. FIG. 2B shows curves 104' and 204, which respectively depict the rates of change of curves 100' and 200. Curves 104' and 204 are overlaid on one another, and it can be seen that both are identical to curve 104 of FIG. 1. Therefore, the continuous monotherapy does nothing to temper the magnitude of the transient change in blood pressure caused by the MBPS.

Figure 3A:
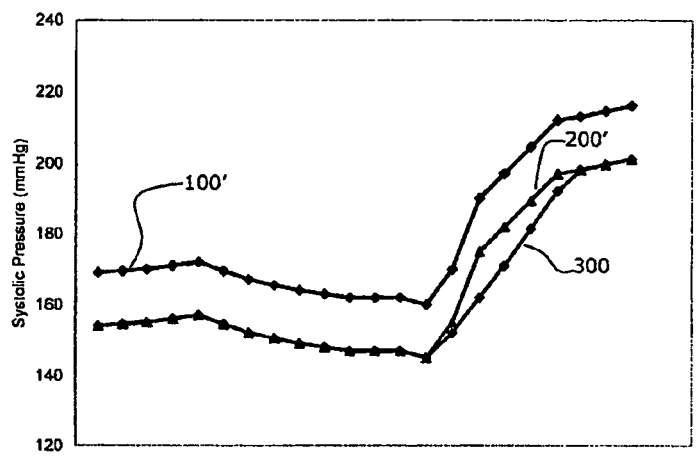
FIGS. 3A-3C illustrate the effect of a special electrotherapy program that administers a modulated electrotherapy dose that is designed to increase the level of pressure-reducing therapy during the MBPS according to one aspect of the invention.
Figure 3B:
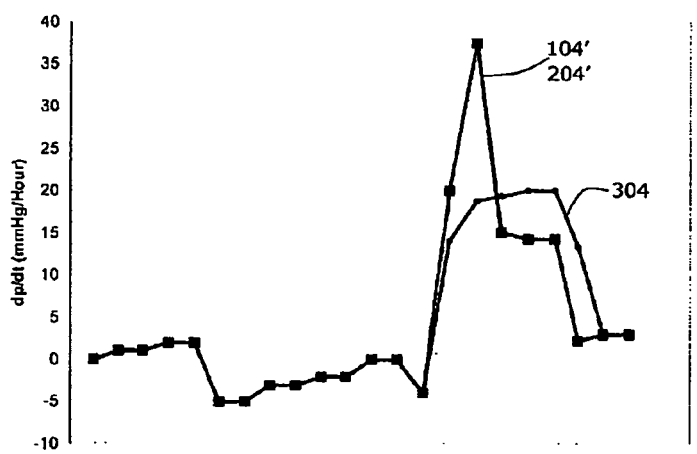
Figure 3C:
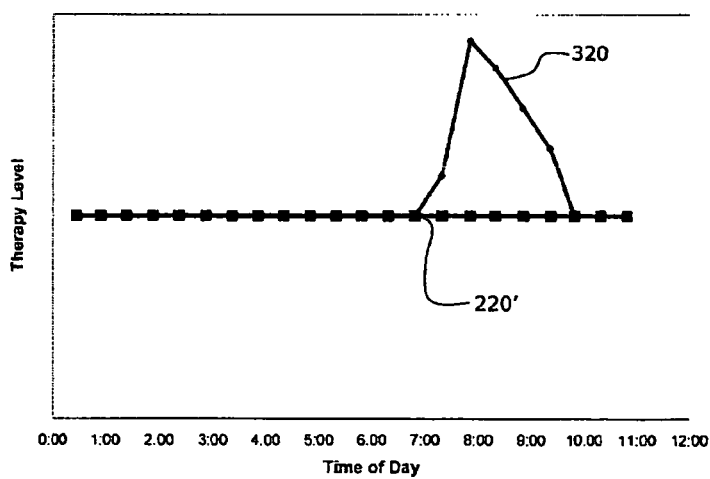

FIGS. 3A-3C illustrate the effect of a special electrotherapy program that administers a modulated electrotherapy dose that is designed to increase the level of pressure-reducing therapy during the MBPS. FIG. 3A shows three blood pressure curves: curve 100'; curve 200', which is identical to curve 200 of FIG. 2A and repeated in FIG. 3A for reference; and curve 300, which is the blood pressure pattern achieved by administering modulated electrotherapy having a profile depicted by therapy curve 320 of FIG. 3C. For reference, FIG. 3C also shows therapy level curve 220', which is identical to therapy level curve 220 of FIG. 2C. Referring again to FIG. 3A, blood pressure curve 300 has the same pre-surge and post-surge levels as curve 200', but has a more steady rate of change during the MBPS that peaks at slightly greater than one-half of the rate of change of curve 200'. This result is depicted in FIG. 3B. Curve 304 represents the rate of change of curve 300. For reference, curves 104' and 204' are also shown. Curve 204' is identical to curve 204 of FIG. 2B.

Figure 4A:
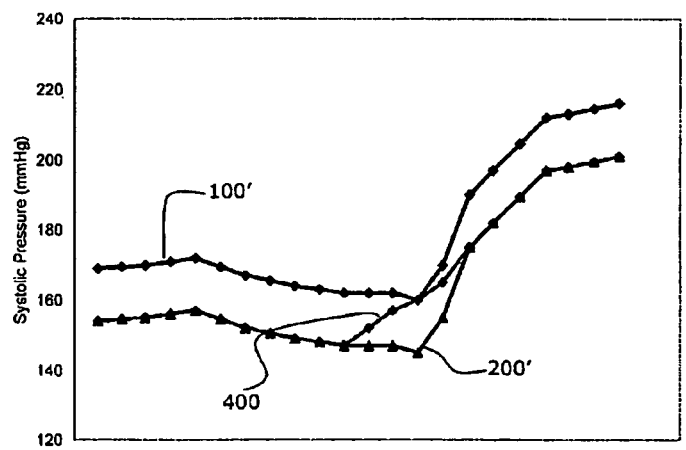
FIGS. 4A-4C illustrate a related technique for blunting the MBPS instantaneous rates of change, in which the dosage of electrotherapy is reduced during a time interval preceding the onset of the MBPS according to one aspect of the invention.
Figure 4B:
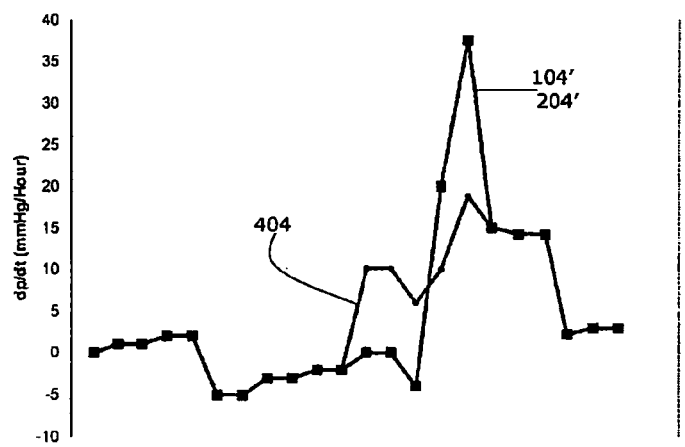
Figure 4C:
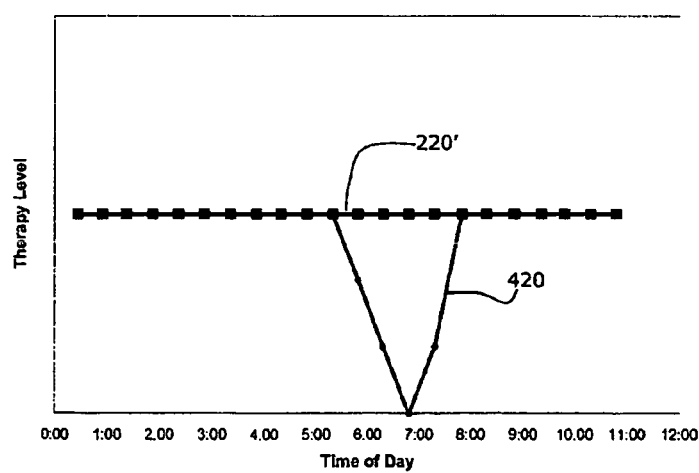

FIGS. 4A-4C illustrate a related technique for blunting the MBPS instantaneous rates of change. Instead of increasing the dosage of the pressure-reducing electrotherapy during the surge as with the technique of FIGS. 3A through 3C, the technique of FIGS. 4A through 4C involves reducing the dosage of the pressure-reducing electrotherapy during a time period prior to the start of the surge. Referring first to FIG. 4C, special electrotherapy program curve 420 is shown superimposed over electrotherapy curve 220'. Electrotherapy curve 420 follows a profile in which, starting at around 5:15, the therapy dose is progressively cut back, and then progressively increased back to its nominal level such that the therapy is returned to its nominal level shortly after the start of the MBPS. The effect of the therapy profile having curve 420 is illustrated by blood pressure curve 400 of FIG. 4A. Curve 400 has a more linear profile for the blood pressure increase than reference curves 100' and 200'. Also, the starting point of the pressure increase occurs earlier than for curves 100' and 200'. In FIG. 4B, curve 404 represents the rate of change of curve 400. Curve 404 peaks at a level that is approximately one-half that of reference curves 104' and 204'.

Figure 5A:
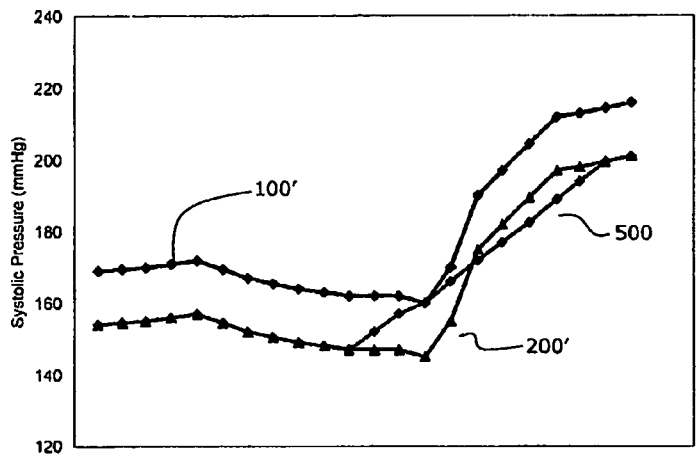
FIGS. 5A-5C illustrate the effects on the patient's systolic blood pressure curve of applying a special electrotherapy program that includes both the therapy dosage level decrease preceding the natural start of the morning surge as illustrated in FIGS. 4A-4C, and a therapy level increase following the start of the morning surge as illustrated in FIGS. 3A-3C.
Figure 5B:
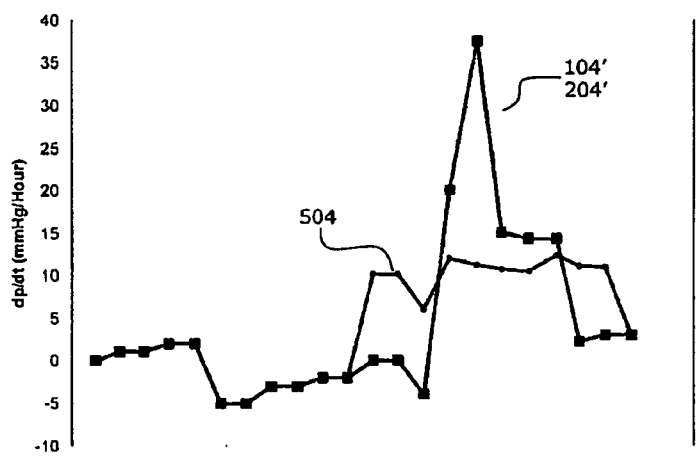
Figure 5C:
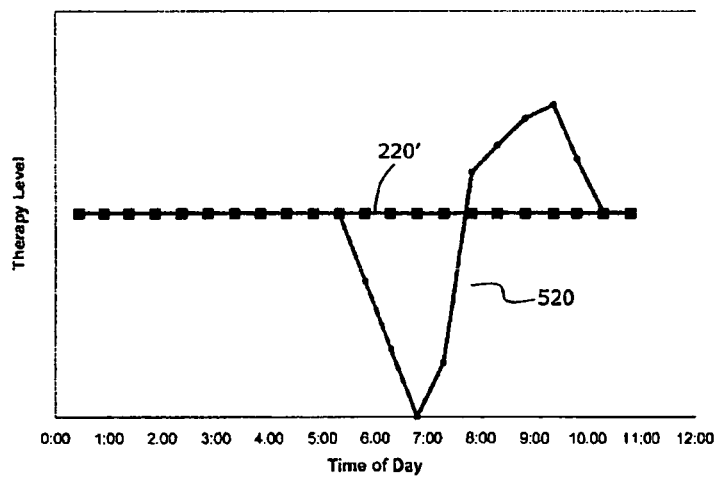

FIGS. 5A-5C illustrate the effects on the patient's systolic blood pressure curve of applying a special electrotherapy program that includes both the therapy dosage level decrease preceding the natural start of the morning surge as described with reference to FIGS. 4A-4C, and a therapy level increase following the start of the morning surge as described above with reference to FIGS. 3A-3C. This therapy profile is illustrated in FIG. 5C. Therapy program curve 520 shows a period of reduced therapy level followed immediately by a period of increased therapy level. Curve 500 of FIG. 5A illustrates the result on the patient's blood pressure over time. Resulting blood pressure curve 500 has a substantially linear pressure increase that begins before the naturally-occurring start of the MBPS and ends by merging into curve 200' to arrive at the blood pressure level at the conclusion of the MBPS. FIG. 5B shows curve 504, which illustrates the rate of change of curve 500. Curve 504 has a peak level that is around one-third the peak level of reference curves 104' and 204'.

Figure 6:
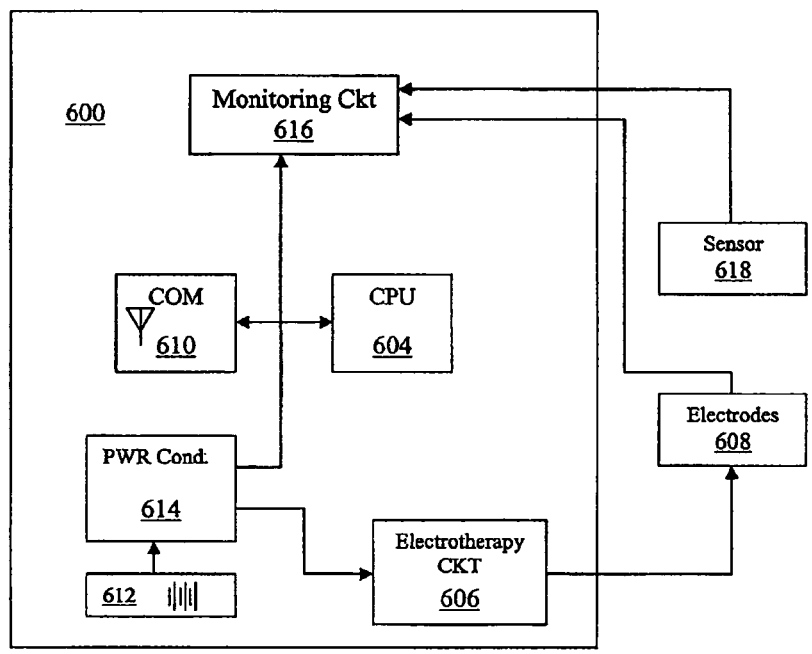
FIG. 6 is a diagram illustrating various components of an example baroreflex activation device according to one aspect of the invention that is implanted in a patient.

FIG. 6 is a diagram illustrating an example baroreflex activation device 600 that is implanted in a patient 602. Implanted device 600 includes a central processor unit (CPU) 604, which may include one or more microprocessors or microcontrollers, for example, that is configured to control the operation of the device. CPU 604 is configured to cause the device to administer the electrotherapy via electrotherapy circuit 606 and electrodes 608. A communications circuit 610 is interfaced with CPU 604 and is used for communicating information between CPU 604 and equipment external to the patient 602, such as a device programmer (not shown). Baroreflex activation device 600 also includes a power source such as a battery 612, and power conditioning circuitry 614 for converting the battery power into various power supplies suitable for powering each sub-system of the device. Optionally, CPU 604 can detect at least one physiologic condition of patient 602 via patient monitoring circuitry 616 and at least one sensor 618.

Figure 7:
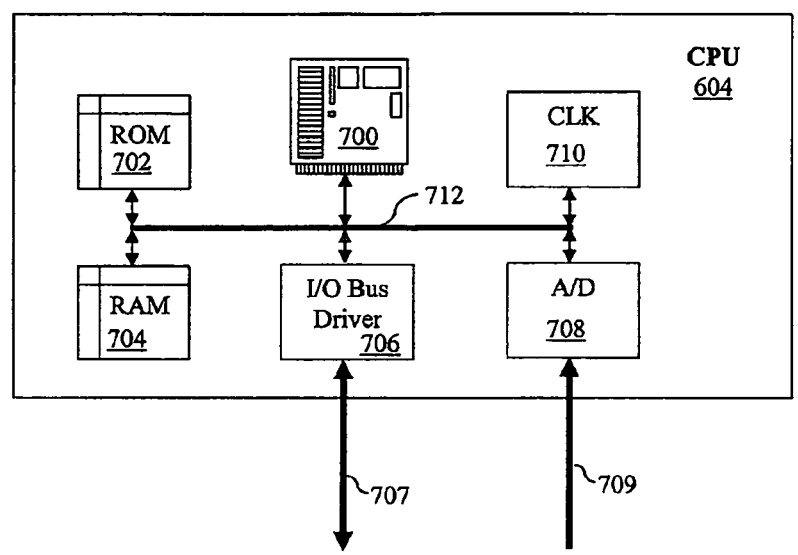
FIG. 7 illustrates one embodiment of a central processing unit (CPU) of the baroreflex activation device of FIG. 6.

FIG. 7 illustrates one embodiment of CPU 604. CPU 604 includes a microprocessor core 700; read-only memory (ROM) 702 for storing instructions; random access memory (RAM) 704 for use as data gathering, or scratchpad memory during operation; input/output (I/O) bus driving circuitry 706 for transmitting and receiving information via, and controlling the use of, I/O bus 707; analog-to-digital (A/D) converter 708 for converting analog signals received via analog inputs 709 into a digital format for use by microprocessor core 700; and clock 710 for providing a time base for use by microprocessor core 700. An internal CPU interconnect 712 provides an interface between the various CPU components, and can include conventional data exchange hardware, such as a data bus, an address bus, and control lines (not shown).

In one embodiment, the clock 710 is a real-time clock (RTC) that keeps track of day, date, and time, including year, month, hour, minutes, and seconds, and feeds this time information to microprocessor core 700 when prompted. In one embodiment, clock 710 simply provides a reliable timer that enables CPU 604 to generally monitor the passage of time. Microprocessor core 700 can utilize the simple time base information provided via clock 710 to calculate the time of day, date, day of the week, or time duration since a particular event. In turn, this calculated time information can be used by the microprocessor core 700 to determine the starting time of the expected blood pressure rise of the patient incident to an expected increase in the patient's activity level. Preferably, clock 710 and/or CPU 604 keeps track of the day of the week in addition to the time of day. For example, in treating a patient who is on a Monday-Friday work schedule, the blood pressure surges on Monday-Friday mornings may be treated differently (such as more aggressively) than morning surges on weekends. Similarly, keeping track of the days of the week would enable treating Monday morning surges more aggressively than Tuesday-Friday surges, for example. Alternatively, CPU 604 may also keep track of days of month/year to adjust for holidays, daylight savings time, seasonal changes, and the like.

A baroreflex activation device according to one embodiment of the invention does not require a hemodynamic monitoring sub-system to detect an indication for applying increased or decreased dosage levels of electrotherapy. According to one embodiment, a hypertension treatment device implanted in a patient includes a time base clock. One embodiment of the time base clock is a real-time clock circuit that is configured to represent at least the time of day. Preferably, the time base clock can also represent the day of the week. The device is configured with a first transition time setting at which the patient is anticipated to transition from a state of relative inactivity to a state of relatively higher activity. In operation, the device executes a special electrotherapy program during a time window proximate in time to the first transition time setting. Preferably, the start of the time window precedes the first transition time setting, and the end of the time window succeeds the first transition time setting. In this regard, one embodiment responds proactively to an expectation, prediction, or, generally, to an anticipation of a future MBPS by initiating the special electrotherapy program before the actual start of the MBPS.

The special electrotherapy program causes the device to selectively apply electrostimulation such that the patient's blood pressure rises relatively gradually in response to a low-to-high activity level transition occurring proximately in time to the first transition time setting. The relatively gradual blood pressure rise is relative to the rise that would occur in the absence the special electrotherapy program, and can be achieved by reducing the difference between the low-pressure and high-pressure levels, by extending the time duration during which the blood pressure rise occurs, or by a combination thereof.

Figure 8:
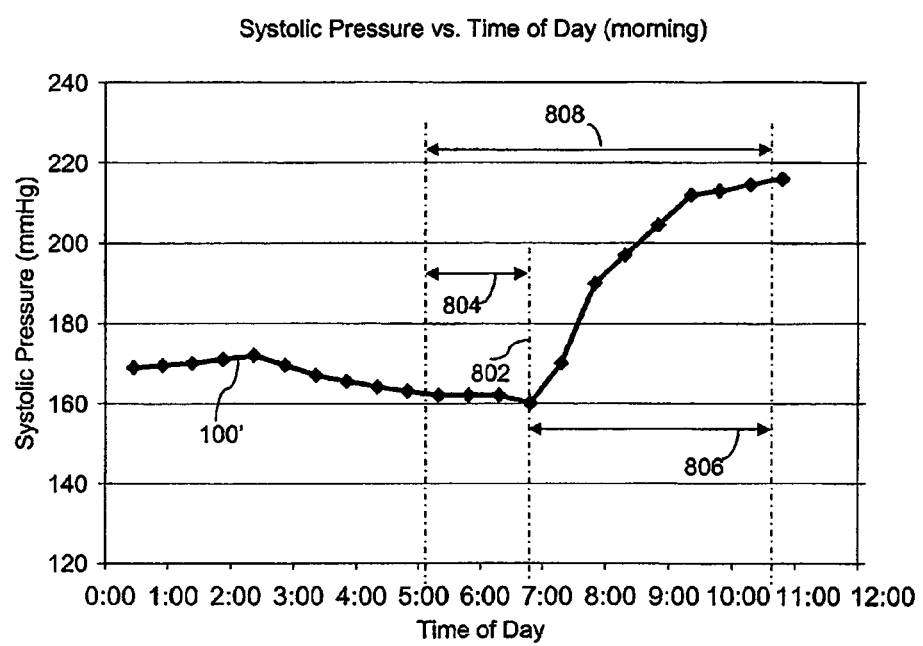
FIG. 8 illustrates an example time window positioned around the transition time of a MBPS, during which window a special electrotherapy program could be applied according to one aspect of the invention.

FIG. 8 illustrates an example window positioned in time around the transition time of a MBPS, during which window a special electrotherapy program would be applied. FIG. 8 shows reference blood pressure curve 100', which represents a patient's MBPS beginning at just before 7:00, as indicated at time 802. As described above with reference to FIGS. 3A-5C, various MBPS management schemes according to embodiments of the invention include special electrotherapy programs that can be administered during the transition window that includes: (a) a pre-surge time interval 804 that precedes the start of the surge (at time 802) by a predetermined duration; (b) a post-surge time interval 806 that begins at the surge start time 802 and lasts for a predetermined duration; or (c) during a combined pre- and post-surge time interval 808 that includes both intervals 804 and 806.

Figure 9A:
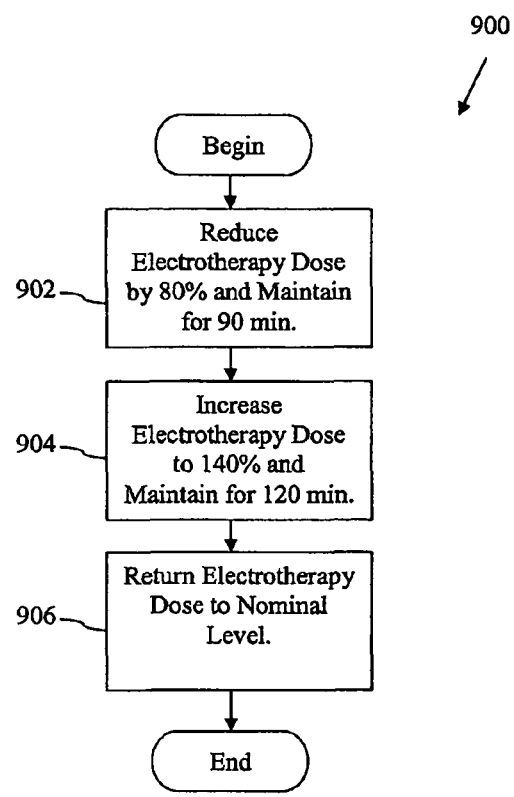
FIGS. 9A and 9B illustrate examples of special electrotherapy program process flows according to various embodiments of the invention.

During pre- and post-surge intervals 804 and 806, respectively, the special electrotherapy program preferably applies different dosages of electrotherapy to reduce the peaks of the instantaneous changes in blood pressure. FIG. 9A illustrates an example special electrotherapy program process 900. Process 900 begins at the start of interval 804. A supervisory process that initiates special electrotherapy program process 900 is described below with reference to FIG. 10. Special electrotherapy program process 900 is time-based in the sense that each electrotherapy administration step of the process is maintained for a predetermined length of time. Also, persons skilled in the relevant arts will appreciate that the electrotherapy dosages and durations of the process steps, as well as the number of process steps can be varied within the spirit of the invention.

Process 900 begins when a nominal electrotherapy program is being applied. The nominal electrotherapy program is typically a fixed dosage selected to provide a generally steady reduction of the patient's blood pressure; however, the nominal electrotherapy program can be a variable dosage that is adjustable or dynamically controllable based on the circumstances. In one embodiment, the nominal electrotherapy program applied by the implanted baroreflex activation device provides at least two nominal electrotherapy dosages, such as one nominal dosage for periods of relative inactivity of the patient (such as sleep), and one for periods of relatively higher activity levels. There can be other nominal dosages for various periods of intermediate activity levels. Essentially, however, in the present context, the nominal electrotherapy program refers to the output of the implanted baroreflex activation device in the absence of any blood pressure surges.

At step 902 of process 900, the electrotherapy is reduced from the nominal (e.g., sleep time) dosage by a factor of 80%, for example, and maintained for 90 minutes. At step 904, the electrotherapy is sharply increased to 140%, for example, of the nominal (e.g., awake time) dosage. Step 904 is preferably timed to coincide with the patient's activity level transition time (i.e. shortly before the patient wakes up). At step 906, the electrotherapy dosage is returned to its nominal (e.g. awake time) level(s) following the expected duration of the MBPS. Process 900 is designed to reduce the magnitude and slope of the MBPS by first causing the patient's blood pressure to increase during the pre-surge interval, and then by reducing the magnitude of the final level of the MBPS. Additionally, process 900 is design to blunt the MBPS by administering aggressive electrotherapy during the surge.

Figure 9B:
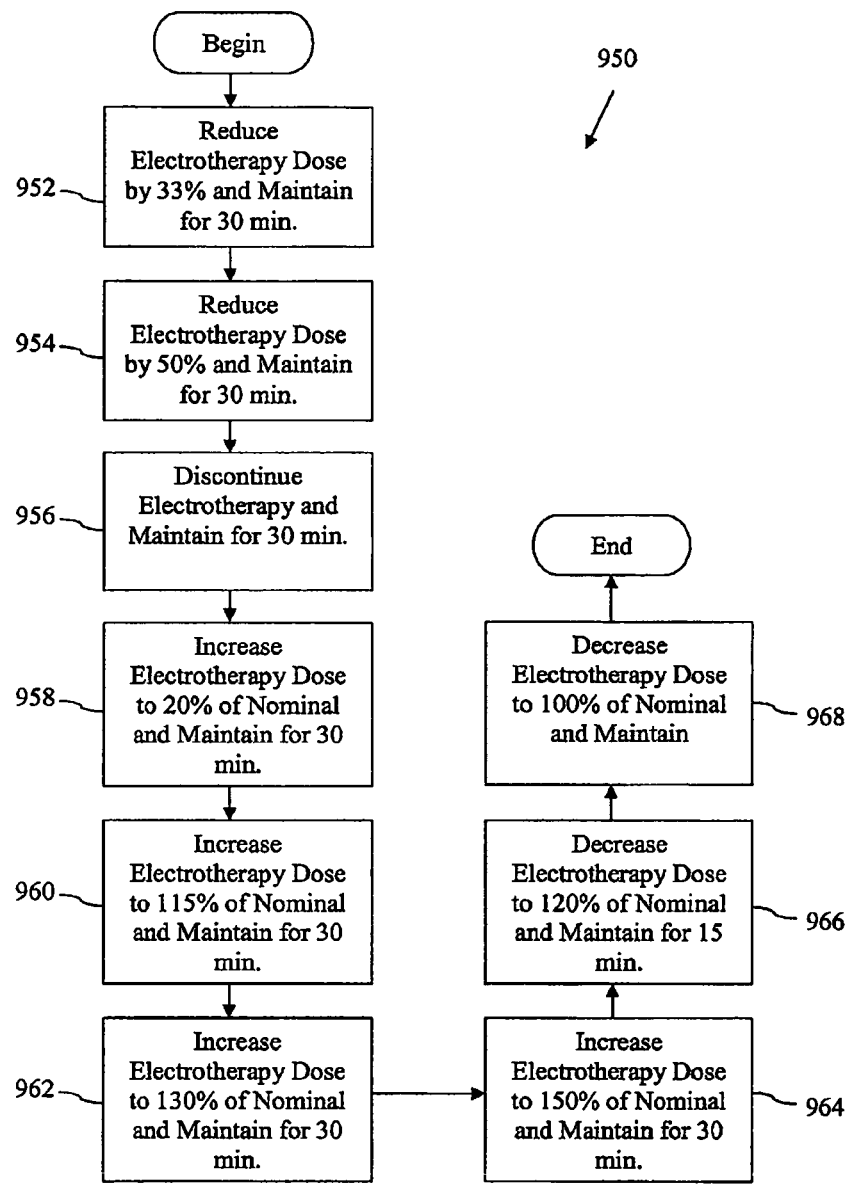

FIG. 9B illustrates special electrotherapy process 950, which is a variation of process 900. In process 950, control of the patients blood pressure is achieved with finer granularity. At step 952, the nominal electrotherapy dosage is reduced by 33% and maintained for 30 minutes. At step 954, the dosage is further reduced by 50% and maintained for 30 minutes. At 956, the electrotherapy is discontinued entirely, and this state is maintained for 30 minutes. At step 958, the electrotherapy is re-administered at the low level of 20% of the nominal dosage. During these steps, the electrotherapy has been cut back to permit the patient's blood pressure to rise gradually in a controlled manner. As a variant of this embodiment, pressure-increasing electrotherapy can be applied to force the patient's blood pressure to increase in a controlled manner.

At step 960, the electrotherapy is increased sharply to 115% of the nominal level, and maintained for 30 minutes. Step 960 is timed such that the start of the MBPS occurs during the 30-minute period. At steps 962 and 964, the electrotherapy is further increased sequentially to 140% and 150% of nominal to aggressively counter-act the pressure rise of the MBPS. At step 966, timed to be executed towards the end of the MBPS, the aggressive electrotherapy dose is cut back to about 120% of nominal. At step 968, the aggressive electrotherapy dosage is further cut back to the nominal level to permit the patient's blood pressure to stabilize at the final, post-MBPS, level. In one embodiment, the stepwise sequence of process 950 has therapy dosage levels and time durations such that the controlled MBPS is gradual and has a generally constant slope.

Figure 10:
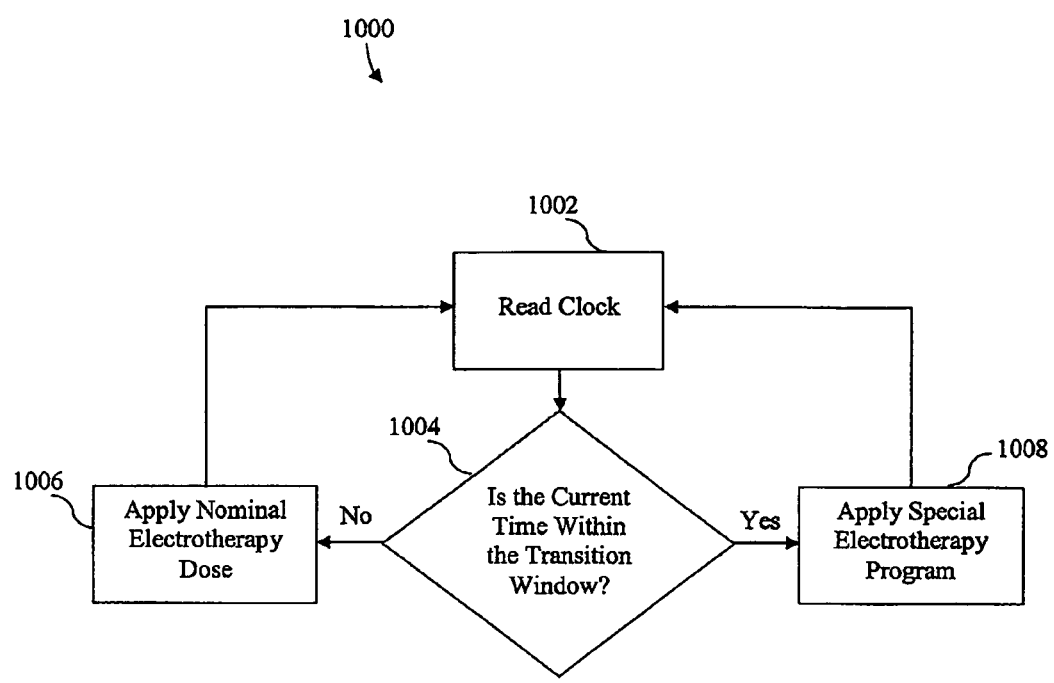
FIG. 10 illustrates an example supervisory operating process for an implanted baroreflex activation device according to one embodiment that determines when to apply the special electrotherapy program and when to apply a nominal electrotherapy dose based on the time.

FIG. 10 illustrates an example supervisory operating process 1000 for an implanted baroreflex activation device that determines when to apply the special electrotherapy program and when to apply a nominal electrotherapy dose based on the time. At 1002, the CPU of the device reads the clock to determine the current time. In this context, the current time can be the time of day, or a duration of time lapse since a particular reference time or event. At 1004, the CPU determines whether the current time is within the pre-defined window associated with the transition window. If the blood pressure is outside of the window, the nominal electrotherapy dose or program is applied, as indicated at 1006. If, on the other hand, the current time is within the pre-defined transition window, the special electrotherapy program is applied, as indicated at 1008.

Referring again to FIG. 8, the transition window 804, 806, or 808 can be set by a variety of techniques. According to one embodiment, the transition window is set in the implanted baroreflex activation device by an external device programmer that has a transceiver capable of communicating with a matching transceiver of the implanted device. Preferably, the external programmer has a simple time-setting function that can be operated by the patient. For example, the external programmer can be part of an alarm clock, GPS receiver, personal digital assistant (PDA), cellular telephone, or other common appliance. The wakeup time setting in the appliance is communicated to the implanted device and treated as the anticipated wake-up time. The beginning and end times of the transition window are then established around the anticipated wake-up time.

In a related embodiment, the implanted baroreflex device includes a feature that enables at least a portion of the special electrotherapy program to be disabled. For example, if the patient expects to sleep in, travel, or otherwise deviate from the patient's usual routine, the patient can use an external programmer or other device for communicating a signal to the implanted baroreflex activation device (such as a magnet). In response to the disable command, the special electrotherapy program can be adjusted to cancel the function that anticipates the occurrence of the MBPS, for example.

In a related embodiment, the external programmer programs the wakeup time set point into the implanted baroreflex activation device soon after the set-point is entered into the programmer by the patient. The implanted device uses its time base clock to recognize the start of the transition window as the current time approaches the wake-up time. In a first variation of this embodiment, the external programmer keeps track of the wake-up time set point and the current time, and signals to the implanted device when the time of the start of the transition window has been reached. In this first variation embodiment, the implanted device does not require a time base clock because the timing of the transition window is taken care of by the external programmer (which is presumed to be within communications range of the implanted device at least during the execution of the special electrotherapy program). In a second variation embodiment, both, the external programmer, and the implanted device keep track of the current time and compare the current time against the wake-up set point. Prior to initiating the special electrotherapy program, the implanted device and external programmer communicate with one another to confirm that the special electrotherapy program is to be executed at the correct time in view of the wake-up time set point and current time reading.

If necessary, the time base clock in the implanted device can be adjusted by using the external programmer, which may be optionally connected to a networked time source such as the Internet, GPS, or radio stations. If the patient should change locations, the time base clock could be updated according to the local time settings.

According to one aspect of the invention, a hypertension treatment system including an implantable baroreflex activation sub-system further includes a physiologic monitoring sub-system that can communicate with the implantable baroreflex activation sub-system. The physiologic monitoring sub-system generally includes at least one sensor, and monitoring circuitry that is interfaced with the sensor. The at least one sensor detects and/or measures a physiologic condition of the patient; the monitoring circuitry powers the sensor (if needed), reads the sensor, and output a signal representing the sensor reading.

In various embodiments, different sensors and different combinations of sensors are used. Persons skilled in the relevant arts will appreciate that this aspect of the invention is not limited to any particular sensing technology or arrangement. Examples of sensing include: hemodynamic sensing, motion sensing, temperature sensing, positional sensing, photo sensing, neural activity sensing, and the like. Hemodynamic sensing includes, but is not limited to, heart rate sensing, ECG activity sensing, blood pressure sensing, pulse oxymetry sensing, respiration activity sensing (such as minute respiration), and the like.

The monitoring circuitry includes circuits for receiving sensor output, as well as any signal conditioning or processing circuits for generating an output signal. Certain sensors may require power to be supplied, in which case the corresponding monitoring circuitry will include the appropriate supply power to energize the sensors. In embodiments having multiple different types of sensors, the monitoring circuitry includes, collectively, each corresponding circuitry for each different sensor. In one embodiment, the monitoring circuitry includes analog-to-digital (A/D) conversion, data storage, and data analysis functionality, which can provide information in a summary format as its output. Examples of summary outputs include data aggregation and statistically-analyzed data.

The interface between each sensor and each corresponding monitoring circuitry can take any suitable form within the spirit of this aspect of the invention, without necessarily a 1-1 correspondence. For example, some sensors can be integrally assembled with their respective monitoring circuits; whereas other sensors can be more remote from their corresponding monitoring circuit (e.g., interconnected via cable or wireless communication channel). The output signal from the monitoring circuitry can be in any suitable form for communication with the other hypertension treatment system sub-systems, including, but not limited to, an analog DC voltage or current signal, an analog modulated signal, a discretized analog signal, and/or a digital signal. The output signal can be communicated via any suitable channel or medium, including by electrical conduction, by electromagnetic transmission, by ultrasonic transmission, and the like.

Figure 11A:
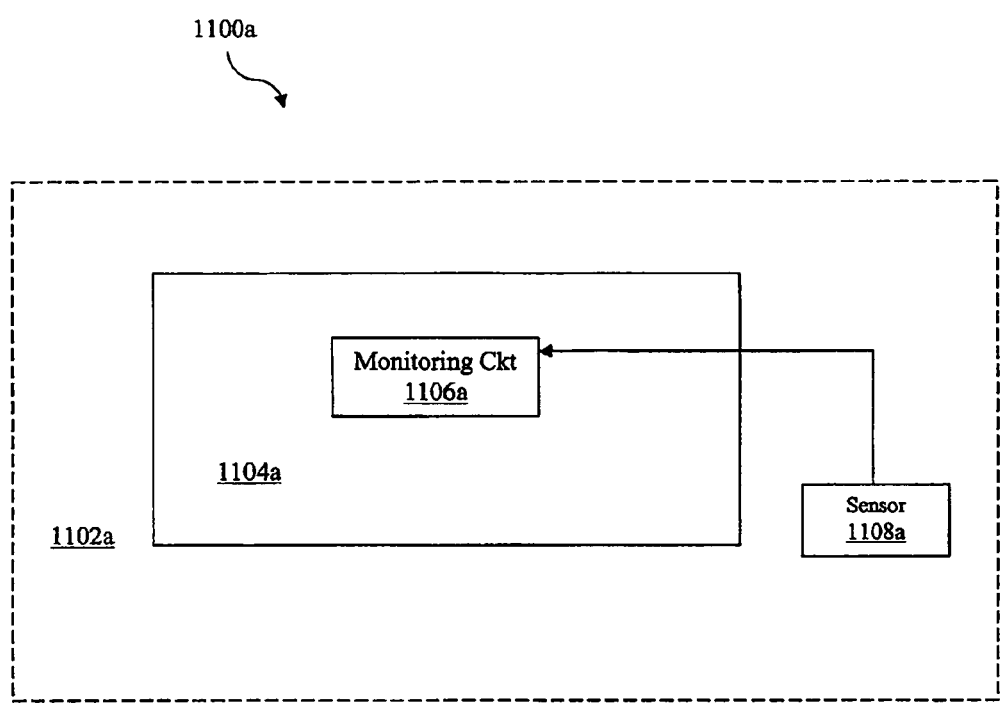
FIGS. 11A-11D are block diagrams illustrating various example configurations of hypertension treatment systems according to various embodiments having physiologic monitoring.

FIGS. 11A-11D are a block diagrams illustrating various example configurations of hypertension treatment systems having physiologic monitoring. Referring to FIG. 11A, hypertension treatment system 1100a includes baroreflex activation device 1104a implanted in patient 1102a. Monitoring circuit 1106a is integrally a part of implanted baroreflex activation device 1104a. Sensor 1108a, also implanted in patient 1102a, is positioned outside the housing of baroreflex activation device 1104a and electrically interfaced with monitoring circuitry 1106a.

Figure 11B:
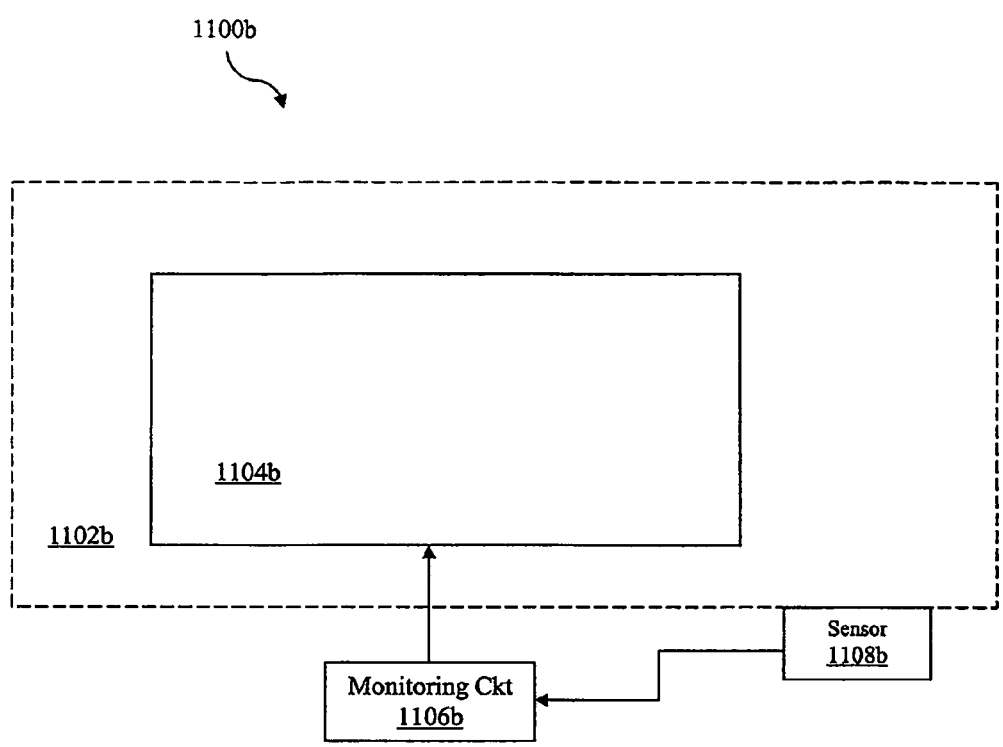

In FIG. 11B, example hypertension treatment system 1100b has an external (i.e. non-implanted) sensor 1110b at the outside surface of the patient 1102b. Baroreflex activation device 1104b is implanted in patient 1102b, and receives sensor information via external monitoring circuitry 1112b. In this embodiment, implanted baroreflex activation device 1104b utilizes a communications circuit (not shown) to receive the output signal from monitoring circuitry 1112b. After receiving the output signal, baroreflex activation device 1104b applies decision-making criteria or control logic functionality to interpret or analyze the sensor reading.

Figure 11C:
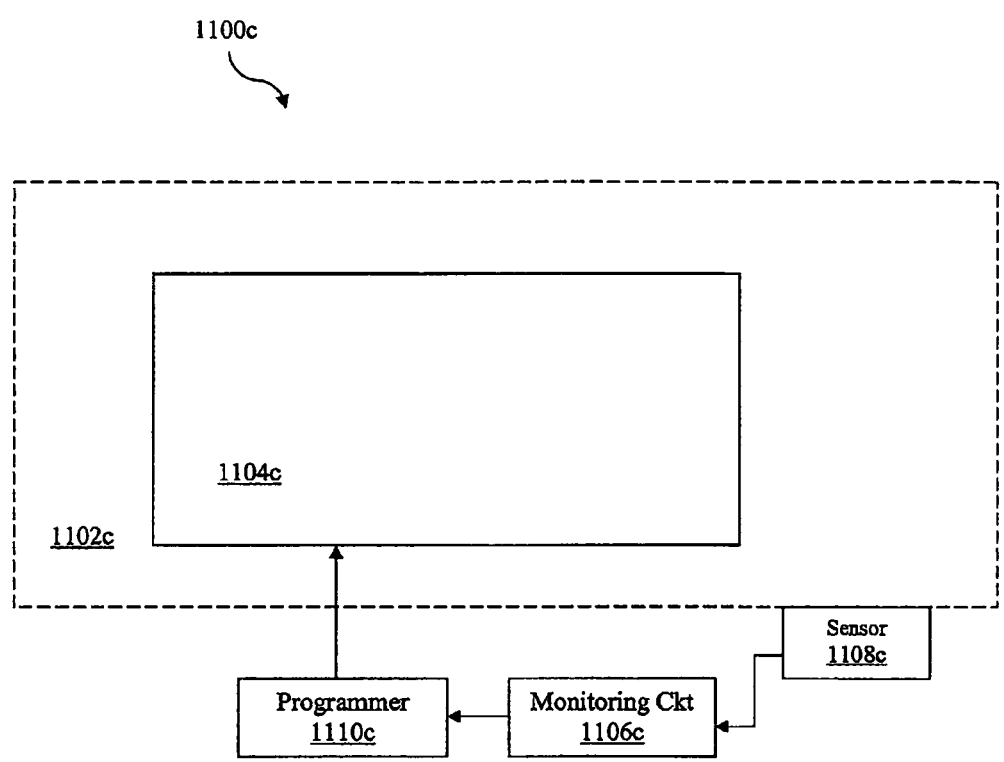

The example arrangement depicted in FIG. 11C includes baroreflex activation device 1104c implanted in patient 1102c. External sensor 1110c reads a physiologic condition of patient 1102c, and feeds the reading to external monitoring circuit 1112c. Sensor data collected via monitoring circuit 1112c is provided to external programmer 1114c for analysis. External programmer 1114c computes operating parameters for implanted baroreflex activation device 1104c, and programs baroreflex activation device 1104c to provide a suitable electrotherapy dosage based on the sensor data. This embodiment differs from the embodiment described above with reference to FIG. 11B in that the present embodiment utilizes an external programmer for analyzing the sensor data, whereas in the embodiment of FIG. 11B, the baroreflex activation device self-programs based on the sensor data.

Figure 11D:
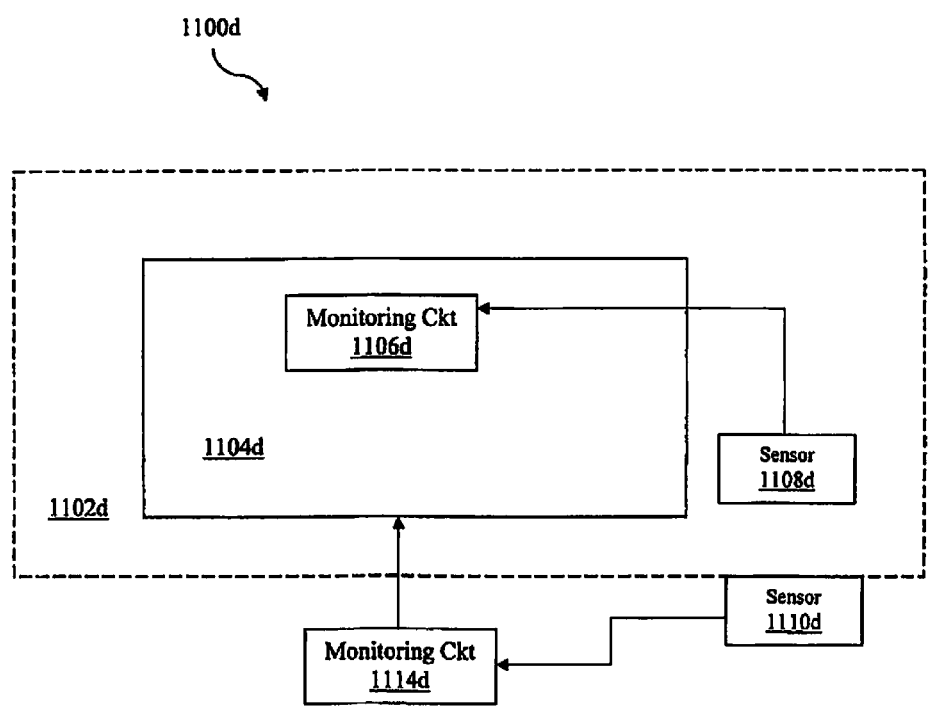

In FIG. 11D, example hypertension treatment system 1100d includes baroreflex activation device 1104d implanted in patient 1102d. Baroreflex activation device 1104d has integral monitoring circuitry 1106d interfaced with implanted sensor 1108d. Also, hypertension treatment system 1100d includes external sensor 1110d interfaced with external monitoring circuitry 1114d. Internal sensor 1108d and external sensor 1110d can be the same, or different types of sensors. Baroreflex activation device 1104d receives sensor information from both monitoring circuits 1106d and 1114d, analyzes the sensor data provided by each, and adjusts its operating point based on the information from the two sensors.

According to one embodiment, the sensor information is used to recognize the MBPS and adjust the baroreflex activation electrotherapy to beneficially control the pressure rise. In a related embodiment, the sensor information is used to characterize patterns of changing activity levels of the patient, enabling the prediction of a future MBPS starting time. In another related embodiment, hemodynamic sensing facilitates characterizing the patient's MBPS curve, which enables predetermining the electrotherapy dosages in the special electrotherapy program applied during and/or before the surge. Preferably, the sensor(s) are designed to work in conjunction with the time-base clock of the hypertension treatment device.

Figure 12A:
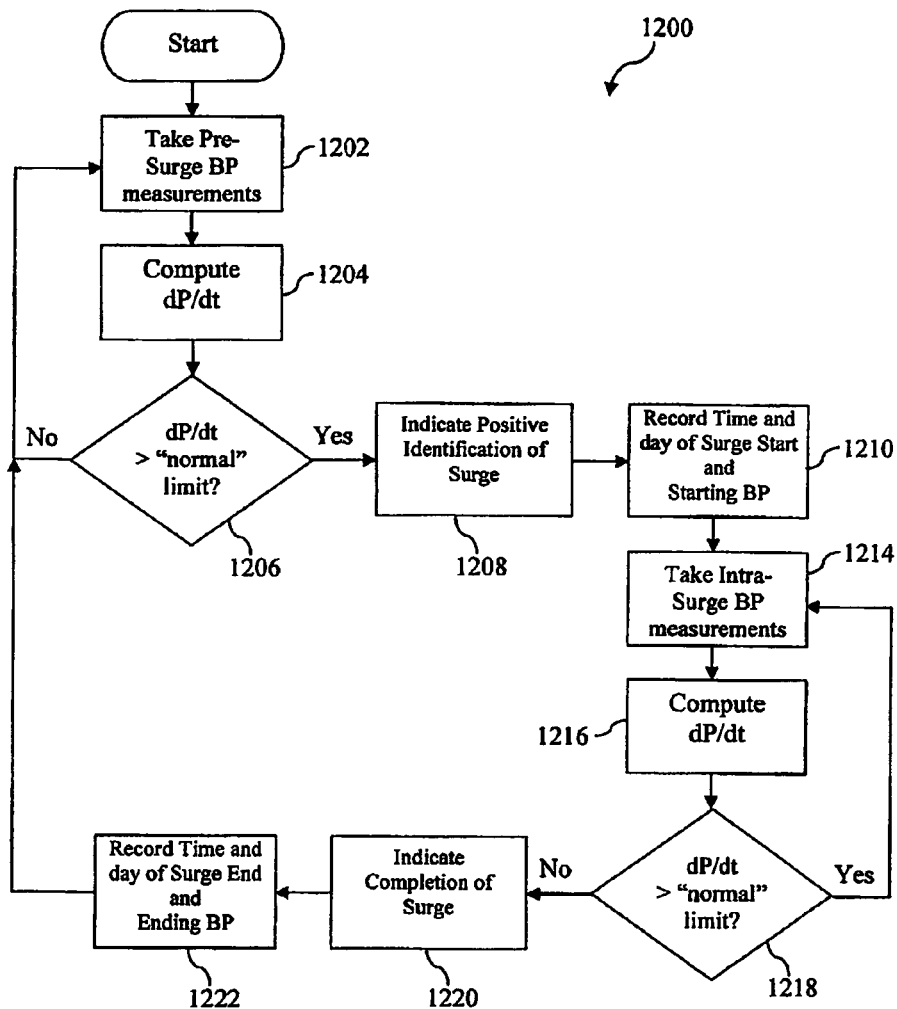
FIG. 12A is a flow diagram illustrating an example process according to one embodiment for recognizing the beginning and end of a blood pressure surge using blood pressure sensing.

FIG. 12A is a flow diagram illustrating an example process 1200 for recognizing the beginning and end of a blood pressure surge using blood pressure sensing. The data gathered by process 1200 can also be used for characterizing the shape of the time-curve of the blood pressure surge. As illustrated, process 1200 begins at a time when there is no blood pressure surge. At step 1202, blood pressure measurements are taken before any surge is recognized. The blood pressure measurements can be taken at predetermined time intervals or otherwise, so long as the time between successive measurements is measured or tracked. At step 1204, the rate of pressure change dP/dt is computed for at least two successive blood pressure measurements. At step 1206, the rate dP/dt is compared against a rate limit for what is deemed to be a normal rate of pressure change. The limit dP/dt is based on the time-rate-of-change of the blood pressure, and can also be based on a magnitude threshold or on a duration threshold such that, for example, dP/dt computations for a very small pressure differential or lasting a very short duration are disregarded.

If the computed dP/dt does not exceed the "normal" limit, then the measurements and computations of steps 1202 and 1204 are repeated. If, however, the computed dP/dt exceeds what is considered a normal rate of variation, the event is considered to be the start of a blood pressure surge, and, at step 1208, the process indicates that a surge has been identified. At step 1210, the time and day, as well as the starting blood pressure value of the surge are recorded. Blood pressure measurements are taken as the surge continues, as indicated at step 1214, and, at step 1216, the rates of pressure changes for these measurements are computed. At 1218, the rate of pressure change is compared against the limit for what is considered normal variation. If the measured dP/dt falls back into the normal range, the completion of the surge is indicated at 1220, and the day, time, and final blood pressure is recorded at step 1222.

In one embodiment, the blood pressure measurements made prior to, during, and following, each surge event, are analyzed for multiple surges. From this analysis, characteristics that are common to all (or most) of the surge events are identified. These common characteristics can include the duration, intensity, dP/dt over time, and other relevant features of the surge events in the patient. In a related embodiment, the common characteristics are used to predict the time of the surge onset. From such information, in a related embodiment, the special electrotherapy program can be manually or automatically adjusted to provide electrotherapy dosage levels, as functions of time, that are especially suited to treat the surges experienced by the patient. These are examples of heuristic learning modes of operation of a hypertension treatment system according to one aspect of the invention.

Figure 12B:
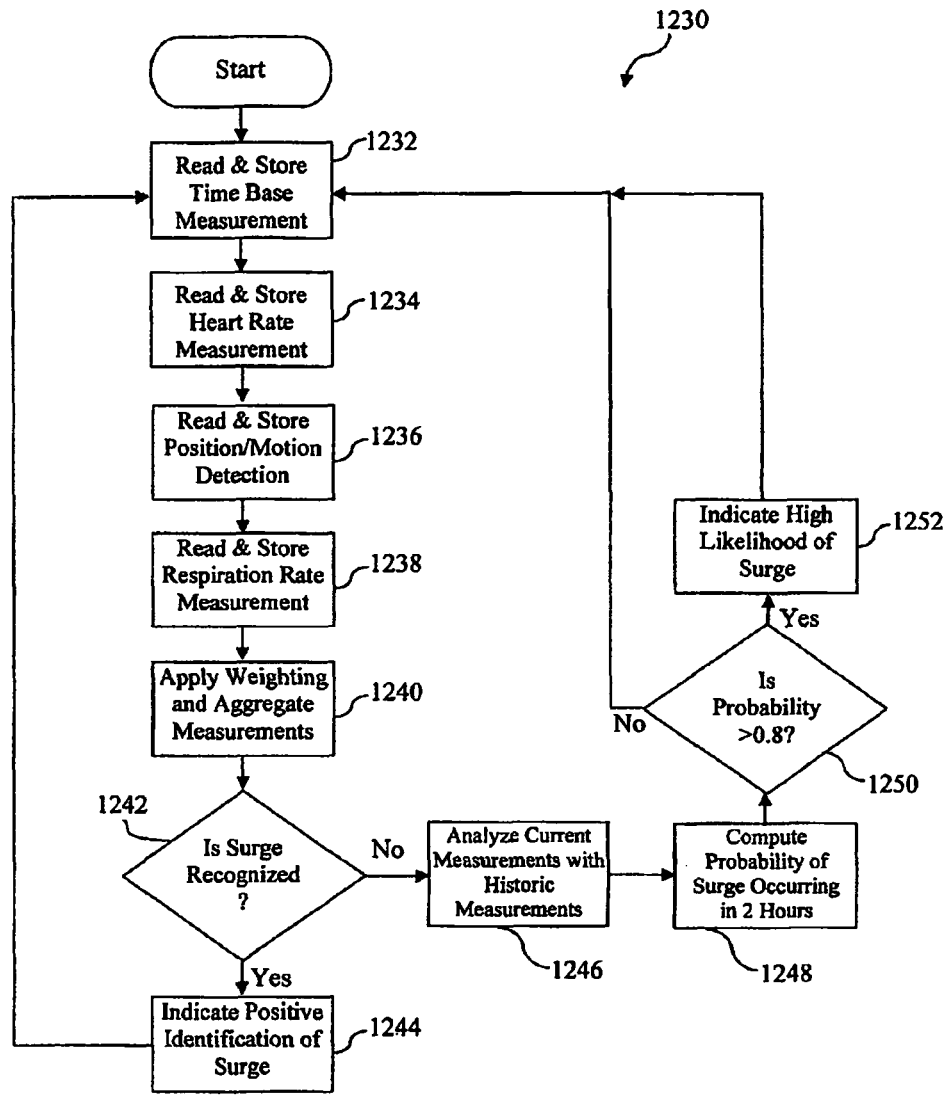
FIG. 12B is a flow diagram illustrating example process according to one embodiment that can recognize and predict blood pressure surges based on a diversity system of sensors.

FIG. 12B is a flow diagram illustrating example process 1230 that can recognize blood pressure surges based on a diversity system of sensors. Process 1230 also includes a function that can predict future occurrences of blood pressure surges. The predictive function is based on using historic records of past surge events, and correlating present-time measurements with historic data trends to develop a probabilistic system of anticipating future blood pressure surge events. At step 1232, the time base measurement is read and stored. The time base measurement can be the time of day, day of week, and the like, in seconds, relative to the calendar or 24-hour clock. The time base measurement can also be an independent time measurement not necessarily synchronized with, or otherwise related to, any external time base.

At steps 1234, 1236, and 1238, physiologic measurements are made. At step 1234, the heart rate is measured and stored. At 1236, the patient's motion and/or position (e.g., lying down, or upright) is read and stored. At 1238, the patient's respiration rate is read and stored. Each of these physiological measurements is indicative of the patient's activity level.

From these measurements, the patient's wake/sleep state can be inferred. When combined with the time base measurement, the duration of any particular activity state can be monitored, and the transition from one type of activity level to another can be detected. Because blood pressure surges are known to accompany sleep-to-wake transitions, the onset of a blood pressure surge can be inferred without the need for a direct blood pressure measurement. For illustrative purposes, these physiologic measurements do not include a direct blood pressure measurement. However, in a related embodiment, a blood pressure measurement can be included among these physiologic measurements for additional patient monitoring accuracy.

Each type of physiologic measurement, and each combination of measurements (including the time-based measurements) may have a different strength of correlation to the patient's actual activity state. Therefore, at step 1240, different weighting is applied to the various measurements, and the weighted measurements are aggregated to produce a basis for inferring the existence of a blood pressure surge event. At step 1242, a logical test is applied to determine whether or not a surge is properly inferred from the physiologic measurements. If a surge is recognized at step 1242, the system provides an indication to that effect, and the physiologic measuring is continued.

If a surge is not recognized according to the logical test applied, the current physiologic measurements are analyzed in light of historic measurements for predicting the onset of a surge event. For example, if the patient is believed to be in a sleep state, the historic duration of the sleep state may suggest an increased likelihood for the surge to occur at about the six-hour mark since the start of the sleep state. Based on a pattern of sleep states, the historic data may indicate that after every seventh extended sleep period, the blood pressure surge is of a higher intensity, suggesting an earlier application of the special electrotherapy program with more aggressive treatment.

The result of the predictive analysis is a probability score. For example, at step 1248, a probability score is computed for the likelihood of surge occurrence in the next two-hour period. If the likelihood is relatively high, such as greater than 80%, as depicted at step 1250, the process returns an indication of a surge prediction at step 1252. If the probability is not sufficiently high to report, the physiologic measurements are re-iterated. The surge prediction can be responded to by initiating the special electrotherapy program to begin permitting the patient's blood pressure to increase prior to the onset of the surge. The surge detection output can be responded to by changing the special electrotherapy program from pre-surge electrotherapy dosages to more aggressive treatment during the surge event.

Methods of predicting, detecting, and characterizing blood pressure surges can be used independently from, or in conjunction with, closed-loop control of the blood pressure surges. Closed-loop surge control utilizes physiologic sensing to continuously feed back information representing the effect of the baroreflex activation electrotherapy to the baroreflex activation device. In this manner, the baroreflex activation device can apply electrotherapy dosage according to a dynamically-adjustable set point to continuously maintain a desired blood pressure commensurate with the patient's activity level.

Figure 13:
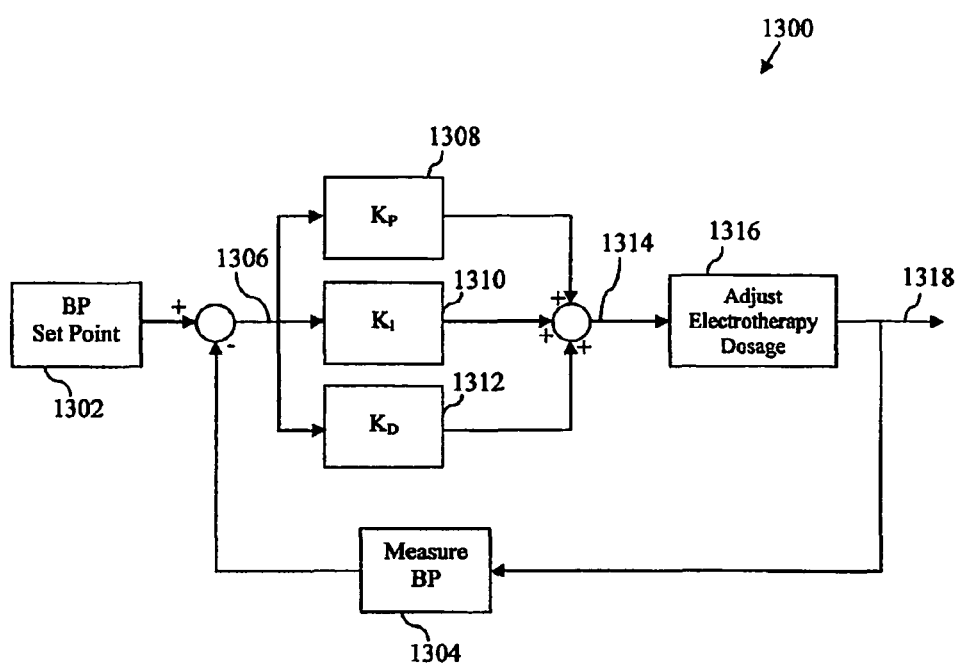
FIG. 13 illustrates an example control system according to one embodiment for regulating the blood pressure, including regulating the rate of change of blood pressure, to prevent rapid changes such as those occurring during MBPS events.

FIG. 13 illustrates an example control system 1300 for regulating the blood pressure, including regulating the rate of change of blood pressure to prevent rapid changes such as those occurring during MBPS events. A blood pressure (BP) set point 1302 is provided to the system. Set point 1302 is a target blood pressure that the system will achieve by adjusting the level of electrotherapy dosage. To achieve a desired rate of change of blood pressure, BP set point 1302 is provided as a function of time representing rate of change that is preferably less than the maximum permissible dP/dt. Thus, set point 1302 can be stable, or time-variable, depending on the circumstances surrounding the surge event.

Control system compares set point 1302 with an actual blood pressure measurement 1304 to produce an error signal 1306. The error signal 1306 is operated on by proportional-integral-differential controls 1308, 1310, and 1312, respectively. Proportional control 1308 includes a proportional weighting constant $K_P$; integral control 1310 includes an integral weighting constant $K_I$; and differential control 1312 includes differential weighting constant $K_D$. The output of each control type is aggregated to produce a control signal 1314. The baroreflex activation device applies an electrotherapy dosage 1316 according to the control signal 1314, which results in a controlled blood pressure 1318 in the patient.

Utilizing a real-time control system such as system 1300 provides dynamic blood pressure and rate of pressure change control that is independent of any deviations in the patient's routine, schedule, or physiology. A preferred embodiment will utilize a combination of: diversity sensing of physiologic indicators to assess activity level; real-time blood pressure measurement; blood pressure surge prediction based on physiology, time, and historic pattern data; and real-time control to regulate pressure according to the special electrotherapy program to blunt the MBPS.

Various modifications to the invention may be apparent to one of skill in the art upon reading this disclosure. Therefore, the above is not contemplated to limit the scope of the present invention.

What is claimed is:

1. An implantable baroreflex activation system for controlling an expected blood pressure surge event, the system comprising:
  at least one electrode;
  an electrotherapy circuit electrically coupled with the at least one electrode;
  a clock; and
  a processor electrically coupled with the electrotherapy circuit and the clock, the processor including operating logic that controls administration of electrotherapy to stimulate baroreceptors of a patient via the electrotherapy circuit and based at least in part on information received from the clock, the processor configured to:
    administer a nominal electrotherapy program during an absence of the expected blood pressure surge event; and
    administer a special electrotherapy program during a predetermined time window, the predetermined time window extending from prior to the expected blood pressure surge event until after conclusion of the expected blood pressure surge event, the special electrotherapy program configured to affect the intrinsic circadian rhythm of the patient by reducing the rate of increase of blood pressure in the patient during the expected blood pressure surge event.

2. The implantable baroreflex activation system of claim 1, further comprising: a physiologic sensor interfaced with the processor; wherein the special electrotherapy program is scheduled in part based on measurements made by the physiologic sensor.

3. The implantable baroreflex activation system of claim 1, further comprising: a physiologic sensor interfaced with the processor; wherein the operating logic includes analysis of stored historical measurements made by the physiologic sensor, wherein the analysis is utilized to predict a future blood pressure surge event.

4. The implantable baroreflex activation system of claim 1, wherein the special electrotherapy program is configured to reduce the rate of increase of blood pressure in a patient during the expected blood pressure surge event by increasing the level of electrotherapy as compared to a level provided during nominal electrotherapy.

5. The implantable baroreflex activation system of claim 1, wherein the special electrotherapy program is configured to reduce the rate of increase of blood pressure in a patient during the expected blood pressure surge event by reducing the level of electrotherapy prior to the expected blood pressure surge event, then subsequent to the start of the expected blood pressure surge event return the level of electrotherapy to a level provided during nominal electrotherapy.

6. The implantable baroreflex activation system of claim 1, wherein the special electrotherapy program is configured to reduce the rate of increase of blood pressure in a patient during the expected blood pressure surge event by reducing the level of electrotherapy prior to the expected blood pressure surge event, then subsequent to the start of the expected blood pressure surge event increase the level of electrotherapy greater than a level provided during nominal electrotherapy, and by the conclusion of the expected blood pressure surge event return the level of electrotherapy to a level provided during nominal electrotherapy.

7. The implantable baroreflex activation system of claim 1, further comprising: a physiologic sensor interfaced with the processor; wherein the predetermined time window is determined at least in part by data collected via the physiologic sensor.

8. A method, comprising:
providing an implantable baroreflex activation system to a user, the implantable baroreflex activation system including:
an electrode;
an electrotherapy circuit electrically coupled with the electrode;
a clock; and
a processor electrically coupled with the electrotherapy circuit and the clock, the processor including operating logic that controls administration of electrotherapy to stimulate baroreceptors of a patient via the electrotherapy circuit and based at least in part on information received from the clock,
providing instructions recorded on a tangible medium to the user that cause the processor to:
administer a nominal electrotherapy program during an absence of an expected blood pressure surge event; and
administer a special electrotherapy program during a predetermined time window, the predetermined time window extending from prior to the expected blood pressure surge event until after conclusion of the expected blood pressure surge event, the special electrotherapy program configured to affect the intrinsic circadian rhythm of the patient by reducing the rate of increase of blood pressure in the patient during the expected blood pressure surge event.

9. The method of claim 8, wherein providing an implantable baroreflex activation system to a user includes causing the implantable baroreflex activation system to be manufactured and made available to the user.

* * * * *